United States Patent [19]

Finke et al.

[11] Patent Number: 4,521,348
[45] Date of Patent: Jun. 4, 1985

[54] PHOSPHORUS-CONTAINING CYANOHYDRINE DERIVATIVES

[75] Inventors: Manfred Finke, Kelkheim; Rainer Mündnich, Frankfurt am Main, both of Fed. Rep. of Germany

[73] Assignee: Hoechst Aktiengesellschaft, Frankfurt am Main, Fed. Rep. of Germany

[21] Appl. No.: 565,850

[22] Filed: Dec. 30, 1983

Related U.S. Application Data

[63] Continuation of Ser. No. 92,456, Nov. 8, 1979, abandoned.

[30] Foreign Application Priority Data

Nov. 11, 1978 [DE] Fed. Rep. of Germany ....... 2849003

[51] Int. Cl.$^3$ .............. C07F 9/32; C07F 9/53; C07C 121/34
[52] U.S. Cl. .............. 260/940; 260/465 F; 260/465.6
[58] Field of Search ............. 260/940, 465 F, 465.6

[56] References Cited

U.S. PATENT DOCUMENTS 2,957,931 10/1960 Hamilton et al. ............. 260/970

FOREIGN PATENT DOCUMENTS 11245 5/1980 European Pat. Off. .
2717440 12/1977 Fed. Rep. of Germany .

OTHER PUBLICATIONS

Bayer et al, "Helvetica Chimica Acta", vol. 55, No. 25, (1972), pp. 224–238.

*Primary Examiner*—Anton H. Sutto
*Attorney, Agent, or Firm*—Curtis, Morris & Safford

[57] ABSTRACT

Cyanohydrine derivatives of the formula

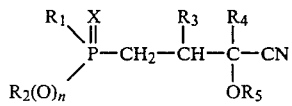

wherein $R_1$ and $R_2$ are alkyl, haloalkyl, cycloalkyl, aralkyl or aryl, $R_3$ and $R_4$ are hydrogen, alkyl, phenyl or benzyl, $R_5$ is hydrogen, acyl, trialkylsilyl or alkoxycarbonyl, X is oxygen or sulfur and n is zero or 1, are intermediates for the manufacture of flame retardants, bactericides, fungicides and herbicides.

2 Claims, No Drawings

PHOSPHORUS-CONTAINING CYANOHYDRINE DERIVATIVES

This application is a continuation of U.S. application Ser. No. 092,456, filed Nov. 8, 1979, now abandoned.

Subject of the present invention are novel phosphorus-containing cyanohydrine derivatives of the formula I

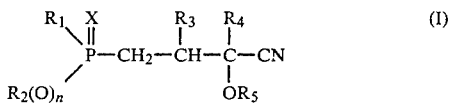

in which
- $R_1$ is $(C_1-C_{12})$-alkyl, halo-$(C_1-C_{12})$-alkyl, $(C_6-C_{10})$-aryl, $(C_7-C_{10})$-aralkyl or $(C_4-C_{10})$-cycloalkyl;
- $R_2$ is $(C_1-C_6)$-alkyl, halo-$(C_1-C_{12})$-alkyl, $(C_6-C_{10})$-aryl, $(C_7-C_{10})$-aralkyl or $(C_4-C_{10})$-cycloalkyl;
- $R_3$ and $R_4$, independently from each other, are hydrogen, $(C_1-C_4)$-alkyl, phenyl or benzyl;
- $R_5$ is hydrogen, $(C_1-C_{12})$-acyl, tri-$(C_1-C_4)$-alkylsilyl or $(C_1-C_6)$-alkoxycarbonyl;
- X is oxygen or sulfur; and
- n is zero or 1.

Subject of the invention is furthermore a process for the preparation of the compounds of formula I, which comprises reacting compounds of the formula II

with compounds of the formula III

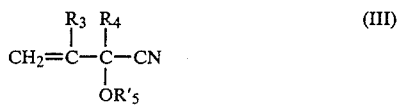

in which $R'_5$ has the meanings of $R_5$ with the exception of hydrogen, in the presence of catalytical amounts of free radical-forming agents, and optionally splitting off the radical $R_5$ in the compounds obtained and/or, in the case of $R_4$ being hydrogen, optionally alkylating the compounds.

In the compounds of the formula II, $R_1$ is preferably lower alkyl, especially methyl or ethyl. "Aryl" preferably means the phenyl radical and "aralkyl" the benzyl radical. By "cycloalkyl" there is to be understood especially cyclopentyl or cyclohexyl. $R_2$ represents preferably lower alkyl, too. "Halo" preferably means chlorine or bromine, which can be present in the alkyl groups of $R_1$ and $R_2$ up to six times.

In the compounds of the formula III, $R_3$ and $R_4$ are above all hydrogen or $(C_1-C_2)$-alkyl. Apart from hydrogen, $R_5$ may stand in principle for any protecting group which can be split off after complete reaction of II with III to form again the free cyanohydrine group. Suitable protecting groups are above all lower acyl groups, especially the acetyl group, furthermore for example the trimethylsilyl, the methoxycarbonyl or ethoxycarbonyl group.

Suitable compounds of the formula II are for example: Methane-phosphonous acid-monomethyl ester, -ethyl ester, -propyl ester, -butyl ester, -isobutyl ester, -hexyl ester, -dodecyl ester, -phenyl ester; ethane-phosphonous acid-monomethyl ester, -ethyl ester, -butyl ester, -hexyl ester; propane-phosphonous acid-monoethyl ester, -butyl ester, -octyl ester; butane-phosphonous acid-monoethyl ester, -butyl ester, -hexyl ester;

phenylphosphonous acid-monomethyl ester, -ethyl ester, -propyl ester, -isobutyl ester;

benzylphosphonous acid-monomethyl ester, -ethyl ester, -propyl ester, -butyl ester;

methylthiophosphonous acid-monomethyl ester, -butyl ester, -2-ethylhexyl ester;

dimethylphosphine oxide, diethylphosphine oxide, dibutylphosphine oxide, diphenylphosphine oxide, methylphenylphosphine oxide, dibenzylphosphine oxide;

dimethylphosphine sulfide, diphenylphosphine sulfide.

The preparation of such phosphonous acid monoesters and secondary phosphine oxides and the analogous thio compounds is known e.g. from Houben-Weyl, Vol. XII/1, p. 193, 212, 320, 331 (1963).

Compounds of the formula III are either known from the literature or can be prepared according to known processes [see Bull. soc. chim. (5), 1, 1317 (1934); Rec. Trav. Chim. Pays-Bas 21, 210 (1902); Acta Chem. Scandinavica 19, 242 (1965); J. Org. Chem. 42, 3956 (1977) and J. F. W. McOmie "Protective Groups in Organic Chemistry" Plenum Press, London 1973, p. 95 et sequ.].

Examples of compounds of the formula III are:

Acroleine-cyanohydrine-formate, -acetate, -propionate, -caproate, -benzoate;

methacroleine-cyanohydrine-formate, -acetate, -propionate, -benzoate;

ethacroleine-cyanohydrine-acetate, -propionate, -benzoate;

phenylacroleine-cyanohydrine-formate, -acetate, -propionate, -benzoate;

methylvinylketone-cyanohydrine-formate, -acetate, -valerate, -caprate, -benzoate;

phenylvinylketone-cyanohydrine-formate, -acetate, -caproate, -benzoate;

(1-cyano-prop-2-enyl)-methyl or ethyl carbonate.

As free radical-forming agents there may be used all compounds which produce free radicals at temperatures in the range of from 50° to 250° C., preferably 100° to 180° C. Examples of such catalysts are:

Di-t-butylperoxide, dipropionylperoxide, dibenzoylperoxide, p-chlorobenzoylperoxide, lauroylperoxide, t-butylperisobutyrate, t-butylperoctoate, t-butylperisononanate, t-butylperacetate, t-butylperpropionate, t-butylperbenzoate, azo-bis-isobutyronitrile, tert. butylhydroperoxide and cumene-hydroperoxide.

Instead of these free radical-forming agents, radiation sources forming such free radicals (UV, Y- or X-rays) may be used.

Generally, the process of the invention is carried out as follows: the unsaturated cyanohydrine derivative of the formula III is added dropwise to the compound of the formula II introduced first into the reaction vessel. In order to prevent undesirable side reactions and to obtain high yields it is advantageous to use an excess of compound II. Preferably no solvent is employed; if desired, however, high-boiling solvents such as toluene, xylene, chloro-benzene, dioxan or dimethyl formamide may be used.

The catalyst which may be one or a mixture of two or more of the above free radical-forming agents is generally added together with the unsaturated cyanohydrine derivative III in an amount of from 0.1 to 10, preferably 0.5 to 5, mol %, relative to the cyanohydrine derivative III. Alternatively, it may be introduced into the reactor together with the compound II, or added dropwise simultaneously with the cyanohydrine derivative III, optionally in an inert solvent or mixed with a portion of compound II.

The reaction temperatures are from about 50° to 250° C., preferably 100° to 180° C. The reaction time may vary within wide limits; depending on the temperature, the operational conditions and size of the batch, it is from 0.5 to 24 hours.

Normally, the process is carried out at atmospheric pressure, but elevated pressure may also be used. Use of a protective gas, for example nitrogen or argon, is not required for the reaction to succeed, but for safety reasons it is recommended to operate under an inert gas atmosphere.

The process may be carried out continuously or batchwise. The reaction produces the compounds of formula I ($R_5 \neq H$) with good yields. Nonconsumed amounts of the compound II can be easily recovered, for example by distillation, and then reused in the process without further purification. After recovering excess compound II the reaction products are generally obtained in the form of liquids which can be further purified by distillation under reduced pressure. This is unnecessary, however, if they are used as intermediates for further reactions.

In case $R_4$ in the reaction products is hydrogen, an alkylation may follow, which is carried out according to known methods and for which generally known alkylation agents such as alkyl halides (methyl bromide, methyl iodide) or dimethyl sulfate are used. If the end products contain a protective group in $R_5$-position, this may be split off by acidic saponification (McOmie, Protective Groups in Organic Chemistry, London 1973).

The compounds of the formula I prepared in accordance with the process of the invention are novel. They may be used as intermediate products for the manufacture of flameproofing agents or biologically active compounds having bactericidal (Helv. chim. Acta 55, 224 (1972)), fungicidal (Sci. Rep. Meiji Seika Kaisha 13, 34 (1973)), or herbicidal (German Offenlegungsschrift No. 27 17 440) action. Such biologically active compounds are for example phosphorus-containing amino acids, which can be prepared from the compounds of the invention by conversion to the corresponding aminonitriles which are then subjected to acidic or basic saponification. For instance, the compound phosphinothricine described in Helv. chim. Acta 55 (1972), p. 224 et sequ., and German Offenlegungsschrift No. 27 17 440 as bactericide or herbicide may be obtained according to the following scheme:

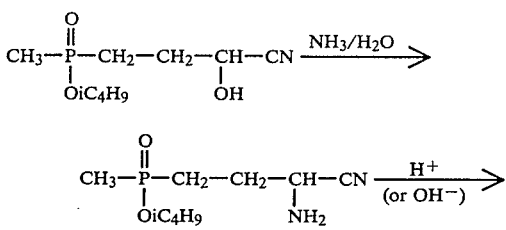

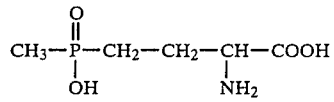

The following Examples illustrate the invention.

EXAMPLE 1

(3-Acetoxy-3-cyano-propyl)-dimethyl-phosphine oxide

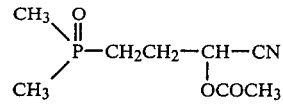

62.5 g of dimethyl-phosphine oxide are heated to 110° C. under a nitrogen atmosphere. 50 g of acroleine-cyanohydrine-acetate containing 4 g of t-butyl peroctoate are added dropwise within about 1 hour while stirring vigourously. After this operation is complete, agitation is continued for another 15 minutes at 115° C., and fractional distillation is then carried out under highly reduced pressure. At 178°–180° C./0.66 mbar 57 g of (3-acetoxy-3-cyanopropyl)-dimethyl-phosphine oxide are obtained (70% of the theory).

EXAMPLE 2

(3-Acetoxy-3-cyano-propyl)-methyl-phosphinic acid methyl ester

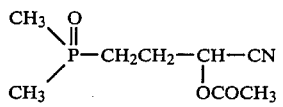

80 g of methanephosphonous acid monomethyl ester are heated to 115° C. under a nitrogen atmosphere. 36 g of acroleine-cyanohydrine-acetate containing 2 g of t-butyl peroctoate are added dropwise within about 1 hour and with vigorous agitation. Agitation is continued for 15 minutes at 120° C., and the reaction solution is fraction distilled under reduced pressure. 58 g of (3-acetoxy-3-cyano-propyl)-methyl-phosphinic acid methyl ester, b.p. 160° C./0.27 mbar, are obtained (92% of the theory).

EXAMPLE 3

(3-Acetoxy-3-cyano-propyl)-methyl-phosphinic acid ethyl ester

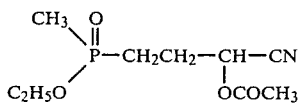

110 g of methanephosphonous acid monoethyl ester are heated to 140° C. under nitrogen protective gas. 50 g of acroleine-cyanohydrine-acetate containing a mixture of 2 g of t-butyl peroctoate and 1 g of t-butyl perbenzoate are added dropwise within about 1 hour and with vigorous agitation. Agitation is continued for 15 minutes at 140° C. Subsequently, the excess methanephosphonous acid monoethyl ester is distilled off under reduced pressure, and then the residue is subjected to fractional distillation under highly reduced pressure. 77 g of (3-acetoxy-3-cyanopropyl)-methyl-phosphinic acid ethyl ester, b.p. 150° C./0.27 mbar, are obtained (83% of the theory).

EXAMPLE 4

(3-Acetoxy-3-cyano-propyl)-methyl-phosphinic acid isobutyl ester

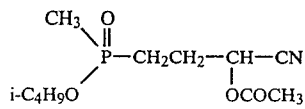

(A) 50 g of acroleine-cyanohydrine-acetate containing 4 g of t-butyl peroctoate are added dropwise within 1 hour and under nitrogen protecting gas to 110 g of methane-phosphonous acid monoisobutyl ester. The addition being complete, agitation is continued for 15 minutes at 120° C., and subsequently, fractional distillation is carried out under highly reduced pressure. 93 g of (3-acetoxy-3-cyanopropyl)-methylphosphinic acid isobutyl ester, b.p. 168°–172° C./0.66 mbar are obtained (89.5% of the theory).

(B) 110 g of methanephosphonous acid monoisobutyl ester are heated to 140° C. under nitrogen protecting gas. 50 g of acroleine-cyanohydrine-acetate containing a mixture of 2 g of t-butyl peroctoate and 1 g of t-butyl perbenzoate are added dropwise within about 1 hour and with vigorous agitation. The addition being complete, agitation is continued for 15 minutes at 140° C. Subsequently, the excess methanephosphonous acid monoisobutyl ester is separated under reduced pressure, and the residue is distilled under highly reduced pressure. 90 g of (3-acetoxy-3-cyanopropyl)-methylphosphinic acid isobutyl ester, b.p. 168°–172° C./0.66 mbar are obtained (87% of the theory).

(C) 50 g of acroleine-cyanohydrine-acetate containing 4 g of t-butyl peroctoate are added dropwise at 130°–135° C. within about 1 hour to 110 g of methanephosphonous acid monoisobutyl ester. Agitation is continued for about 15 minutes at 130° C., and subsequently, fractional distillation is carried out under highly reduced pressure. 92 g of (3-acetoxy-3-cyanopropyl)-methylphosphinic acid isobutyl ester, b.p. 168°–172° C./0.66 mbar are obtained (89% of the theory).

(D) 89 g of methanephosphonous acid monoisobutyl ester are heated to 115° C. under nitrogen protecting gas. 50 g of acroleine-cyanohydrine-acetate containing 4 g of t-butyl peroctoate are added dropwise within about 1 hour and with vigorous agitation. Agitation is continued for 15 minutes at 120° C. Subsequently, the excess methanephosphonous acid monoisobutyl ester is removed under reduced pressure, and the residue is then distilled under highly reduced pressure. 91 g of (3-acetoxy-3-cyanopropyl)-methyl-phosphinic acid isobutyl ester, b.p. 166°–172° C./0.66 mbar, are obtained (87% of the theory).

(E) 110 g of methanephosphonous acid monoisobutyl ester are heated to 145° C. under nitrogen protecting gas. 50 g of acroleine-cyanohydrine-acetate containing 4 g of t-butyl pernonoate are added dropwise within about 1 hour and with vigorous agitation. Agitation is continued for 15 minutes at 140° C. Excess methanephosphonous acid monoisobutyl ester is distilled off under reduced pressure, and the residue is then subjected to fractional distillation under highly reduced pressure. 88 g of (3-acetoxy-3-cyanopropyl)-methyl-phosphinic acid isobutyl ester, b.p. 166°–172° C./0.66 mbar, are obtained (84.5% of the theory).

(F) 914 g of methanephosphonous acid monoisobutyl ester are heated to 115° C. under nitrogen protecting gas. 250 g of acroleine-cyanohydrine-acetate containing 8 g of t-butyl peroctoate are added dropwise within about 2 hours and with vigorous agitation. Agitation is continued for a further 15 minutes at 120° C., and the excess methanephosphonous acid monoisobutyl ester is distilled off subsequently under reduced pressure at a bath temperature of up to 175° C. The residue is distilled at 0.66 mbar via a thin-layer evaporator. 513 g of (3-acetoxy-3-cyanopropyl)-methylphosphinic acid isobutyl ester are obtained (98% of the theory).

EXAMPLE 5

(3-Acetoxy-3-cyano-3-methyl-propyl)-methyl-phosphinic acid isobutyl ester

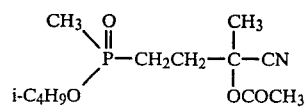

122 g of methanephosphonous acid monoisobutyl ester are heated to 115° C. under nitrogen protecting gas. 40 g of methylvinylketone-cyanohydrine-acetate containing 3 g of t-butyl peroctoate are added dropwise within about 1 hour and with vigorous stirring. Agitation is continued for 15 minutes at 120° C. 39 g of (3-acetocy-3-cyano-3-methyl-propyl)-methylphosphinic acid isobutyl ester (50% of the theory) are obtained in the form of a brown oil. For an analytic test, the product was subjected to distillation under highly reduced pressure (b.p. 164°–172° C./0.54 mbar).

EXAMPLE 6

(3-Acetoxy-3-cyano-2-ethyl-propyl)-methyl-phosphinic acid isobutyl ester

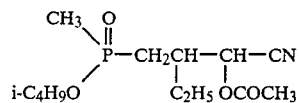

110 g of methanephosphonous acid monoisobutyl ester are heated to 120° C. under nitrogen protecting gas. 60 g of 2-ethylacroleine-cyanohydrine-acetate containing 4 g of t-butyl peroctoate are added dropwise within about 1 hour and under vigorous agitation. Agitation is continued for 15 minutes at 130° C. Subsequently, the excess methanephosphonous acid monoisobutyl ester is removed under reduced pressure, and the residue is then distilled under highly reduced pressure. 73 g of (3-acetoxy-3-cyano-2-ethylpropyl)-methylphosphinic acid isobutyl ester (64% of the theory), distil at 155°–158° C./0.27 mbar.

EXAMPLE 7

(3-Propionyloxy-3-cyano-propyl)-methylphosphinic acid isobutyl ester

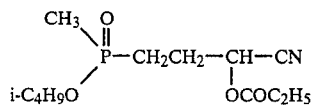

110 g of methanephosphonous acid monoisobutyl ester are heated to 125° C. under nitrogen protecting gas. 50 g of acroleine-cyanohydrine-propionate containing 4 g of t-butyl peroctoate are added dropwise within about 1 hour and with vigorous agitation. Agitation is continued for a further 15 minutes at 120° C. Subsequently, the excess methanephosphonous acid monoisobutyl ester is removed under reduced pressure, and the residue is distilled under highly reduced pressure. 94 g of (3-propionyloxy-3-cyanopropyl)-methylphosphinic acid isobutyl ester (84.5% of the theory), distil at 178°–184° C./0.66 mbar.

EXAMPLE 8

(3-Benzoyloxy-3-cyano-propyl)-methyl-phosphinic acid isobutyl ester

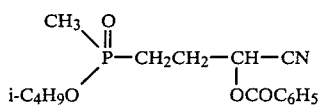

100 g of methanephosphonous acid monoisobutyl ester are heated to 115° C. under nitrogen protecting gas. 47 g of acroleine-cyanohydrine-benzoate containing 4 g of t-butyl peroctoate are added dropwise within about 1 hour and with vigorous agitation. The addition being complete, agitation is continued for 15 minutes at 115° C. Subsequently, the starting materials are distilled off under reduced pressure. 49 g of (3-benzoyloxy-3-cyanopropyl)-methylphosphinic acid isobutyl ester, corresponding to a yield of 60% of the theory, are obtained in the form of a brown oil. The product according to thin-layer chromatography is nearly uniform and in IR spectroscopy has absorption bands at 1748, 2300, 1613, 1190, 719 cm$^{-1}$.

EXAMPLE 9

(3-Acetoxy-3-cyano-propyl)-phenylphosphinic acid ethyl ester

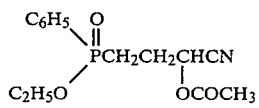

65 g of benzenephosphonous acid monoethyl ester are heated to 130° C. under nitrogen protecting gas. 24 g of acroleine-cyanohydrine-acetate containing a mixture of 1 g of t-butyl peroctoate and 1 g of t-butyl perbenzoate are added dropwise within about 1 hour and with vigorous agitation. The addition being complete, agitation is continued for another 15 minutes at 130° C. Subsequently, the starting substances are distilled off under reduced pressure. 53 g of (3-acetoxy-3-cyanopropyl)-phenylphosphinic acid ethyl ester (53% of the theory) are obtained as a brown oil.

EXAMPLE 10

(3-Acetoxy-3-cyano-propyl)-methyl-thiophosphinic acid isobutyl ester

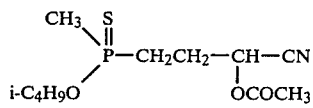

40 g of methanethiophosphonous acid monoisobutyl ester are heated to 115° C. under nitrogen protecting gas. 15 g of acroleine-cyanohydrine-acetate containing 1 g of t-butyl peroctoate are added dropwise within 20 minutes and with vigorous agitation. The addition being complete, agitation is continued for 15 minutes at 120° C. Subsequently, the excess methanethiophosphonous acid isobutyl ester is distilled off under reduced pressure, and the residue is subjected to fractional distillation under highly reduced pressure. 24 g of (3-acetoxy-3-cyanopropyl)-methylthiophosphinic acid isobutyl ester (72% of the theory) distil at 180°–185° C./0.66 mbar.

EXAMPLE 11

(3-Ethoxycarbonyloxy-3-cyano-propyl)-methylphosphinic acid isobutyl ester

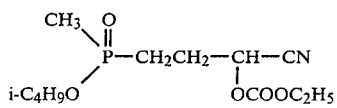

20 g of methanephosphonous acid monoisobutyl ester are heated to 125° C. under nitrogen protecting gas. 30 g of acroleine-cyanohydrine-ethylcaronate containing 2 g of t-butyl peroctoate are added dropwise within about 1 hour and with vigorous agitation. Agitation is continued for 15 minutes at 125° C. Subsequently, the excess methanephosphonous acid monoisobutyl ester is distilled off under reduced pressure, and the residue is subjected to a fractional distillation under highly reduced pressure. 39 g of (3-ethoxycarbonyloxy-3-cyanopropyl)-methylphosphinic acid isobutyl ester (67.5% of the theory) distil at 160°–164° C./0.66 mbar.

What is claimed is:

1. Compounds of the formula I

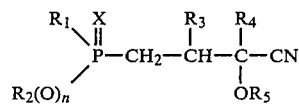

in which
$R_1$ is alkyl;
$R_2$ is alkyl;
$R_3$ and $R_4$, independently from each other, are hydrogen or $(C_1–C_4)$-alkyl;
$R_5$ is acetyl, ethoxycarbonyl, propionyl, or benzoyl;
X is oxygen or sulfur, and
n is zero or 1.

2. Compounds of the formula I

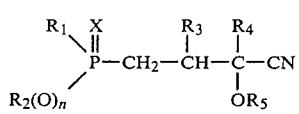

in which
$R_1$ is $(C_1–C_{12})$-alkyl, halo-$(C_1–C_{12})$-alkyl, $(C_6–C_{10})$-aryl, $(C_7–C_{10})$-aralkyl or $(C_4–C_{10})$-cycloalkyl;
$R_2$ is $(C_1–C_6)$-alkyl, halo-$(C_1–C_{12})$-alkyl, $(C_6–C_{10})$-aryl, $(C_7–C_{10})$-aralkyl or $(C_4–C_{10})$-cycloalkyl;
$R_3$ and $R_4$, independently from each other, are hydrogen, $(C_1–C_4)$-alkyl, phenyl or benzyl;
$R_5$ is $(C_1–C_{12})$-acyl, or $(C_1–C_6)$-alkoxycarbonyl;
X is oxygen or sulfur, and
n is zero or 1.

* * * * *